United States Patent [19]
Margel et al.

[11] Patent Number: 6,103,379
[45] Date of Patent: Aug. 15, 2000

[54] PROCESS FOR THE PREPARATION OF MICROSPHERES AND MICROSPHERES MADE THEREBY

[75] Inventors: Shlomo Margel, Rehovot; Hanna Bamnolker, Givataim, both of Israel

[73] Assignee: Bar-Ilan University, Ramat-Gan, Israel

[21] Appl. No.: 08/809,957

[22] PCT Filed: Oct. 5, 1995

[86] PCT No.: PCT/US95/12988

§ 371 Date: Apr. 3, 1997

§ 102(e) Date: Apr. 3, 1997

[87] PCT Pub. No.: WO96/11054

PCT Pub. Date: Apr. 18, 1996

[30] Foreign Application Priority Data

Oct. 6, 1994 [IL] Israel ......................................... 111186

[51] Int. Cl.$^7$ ...................................................... B32B 5/16
[52] U.S. Cl. .................... 428/403; 427/212; 427/222; 427/227; 428/404; 428/407
[58] Field of Search ..................... 428/403, 404, 428/407; 427/212, 213.34, 222, 227

[56] References Cited

U.S. PATENT DOCUMENTS

| | | | |
|---|---|---|---|
| 4,985,166 | 1/1991 | Leising et al. | 252/62.54 |
| 5,108,636 | 4/1992 | Leising et al. | 252/62.54 |
| 5,356,617 | 10/1994 | Schlossman | 424/63 |
| 5,580,655 | 12/1996 | El-Shall et al. | 428/402 |
| 5,585,020 | 12/1996 | Becker et al. | 219/121.85 |
| 5,695,617 | 12/1997 | Graiver et al. | 204/157.41 |
| 5,770,022 | 6/1998 | Chang et al. | 204/164 |
| 5,891,548 | 4/1999 | Graiver et al. | 428/98 |

*Primary Examiner*—Hoa T. Le
*Attorney, Agent, or Firm*—Pitney, Hardin, Kipp & Szuch, LLP

[57] ABSTRACT

A process for the preparation of a microsphere comprising a coating composed of one or more silica nanoparticles layers, comprises the steps of: a) providing a microsphere of polymeric material, the said microsphere having adsorbed on its surface one or more surfactants; and b) causing a layer of silica nanoparticles to coat the surface of the said microsphere by means of seeded polymerization of alkyl silicates onto the surface of said microsphere.

41 Claims, 6 Drawing Sheets

PROCESS FOR THE PREPARATION OF MICROSPHERES AND MICROSPHERES MADE THEREBY

FIELD OF THE INVENTION

The present invention relates to a process for the preparation of microspheres, which may be optionally hollow, and which are consisting of one or more layers of silica shells and may also involve other coatings of different materials, characterized by variety of desirable properties.

BACKGROUND OF THE INVENTION

The preparation of well-defined microspheres of controlled composition is of great importance, because of the potential use of such particles in a wide variety of fields. The complexity of processes for preparing such particles is even greater when the particle to be formed is to be used in delicate biological applications, because then several parameters, which are not easy to handle, should be taken into account, such as types of chemical interactions between the different layers composing the microspheres, as well as the relevant function of the particle within the planned biological application.

Applying coating techniques for polymeric microspheres involves difficulties which do not exist in coating processes of flat surfaces, obviously due to the different physical characteristics of spherical systems. For instance, although techniques based on sol-gel procedures for the preparation of silica are well known [Stober, Fink & Bohn, Colloid Interface Sci. 26, 62 (1968), U.S. Pat. No. 5,272,240], and have been applied successfully for the preparation of a coating for a flat surface [Brinker, Hurd, Schunk, Frye and Ashley, J. of Non-Crystline Solids, 147, 424 (1992); Brinker, Frye, Hurd and Ashley, Thin Solid Films 201. 97 (1991)], the art has failed to disclose a method for coating spherical particles with silica. This silica coating is of great importance because, as will become apparent from the description to follow, it plays a major role in the construction of the desired final microsphere. The silica itself consists of particles the diameter of which is about 50 nm, and is obtained, according to sol-gel procedures, by agents such as tetraethoxysilane, [(SiOEt)4], which are converted, via hydrolysis and subsequent condensation, to silica. With respect to processes for enveloping spherical systems of submicron size, prior art mainly discloses methods for coating inorganic microspheres (made of titania, for example) with polyurea or aluminum oxide [Mayville, Partch and Matijevic, J. Colloid Interface Sci. 120, 135 (1987); Kratohvil and Matijevic, Adv. Ceram. Mater. 2, 798 (1987); Grag and Mateijevic, Langmuir 4, 38 (1988); Aiken and Matijevic, J. Colloid Interface Sci. 126, 243 (1988)]. However, processes described by the prior art, through which organic microspheres are coated, are unsatisfactory and limited, from several aspects: the microsphere is of diameter of only 0.1 µm to 0.3 µm, and is composed only of cationic polystyrene. Furthermore, in all these processes the coating is made of inorganic material, namely, yttrium basic carbonate. Thus, Although hollow yttrium microspheres were further obtained by burning off the core of the described cationic polystyrene coated particles, this characteristic, namely, the inorganic nature of the coating, clearly limits the scope of the fields in which these systems can be applied, Because, as can be learned from the present invention, the interaction between the coating and various ligands is of great importance. The type of the coating plays therefore a major role. [Kawahashi and Matijevic, J. Colloid Interface Sci. 138, 534 (1990); Kawahashi Matijevic, J. Colloid Interface Sci. 143, 103 (1991); Matijevic, Langmuir 10, 8 (1994)].

Another important type of coating is one exhibiting magnetic properties. A method for the preparation of ferrite plating of various chemical compositions is known in the art [Abe et al., J. of Applied Physics 57, pp. 3795–3797, (1985)], yet this method is characterized by several disadvantages and limitations. First of all, an essential condition for the formation of the ferrite film is the presence of hydroxyl groups on the substrate to be coated, because these groups enhance the adhesion of the film to the surface. Furthermore, according to this method, if the microsphere diameter is smaller than 0.5 µm, a continued magnetic coating can not be obtained. Finally, Abe et al. failed to disclose means for the protection of the ferrite coating, in order to avoid a partial leakage of the ferrite into the solution.

The present invention provides processes for the production of microspheres characterized by several desired properties:

a) It provides a process for the preparation of silica coating to spherical particles, wherein surfactants of proper nature, adsorbed on the microspheres, serves as a "connective glue" between the microsphere and the silica nanoparticles;

b) It provides a process for the preparation of a microsphere coated with a magnetic layer;

c) It provides a process for the preparation of hollow silica microspheres;

d) It provides a process for the preparation of magnetic microspheres enveloped with silica layers;

e) It allows a further modification of the surface of the solid or hollow microspheres, which are coated by magnetic layers and silica layers, to adjust them to several biological applications.

SUMMARY OF THE INVENTION

The invention is directed to the preparation and use of microspheres, the diameter of which is in the range of about 0.2 µm up to a few microns, which are made of polymeric materials and contain surfactants of hydrophilic nature on their surfaces. This microspheres are then subjected to further coating stages. The final coated microspheres can then serve in a variety of biological applications. The microspheres can be rendered hollow by removing therefrom the inner polymeric core.

According to the process of the invention the microspheres are obtained by polymerization of monomeric units, such as styrene, chloromethylstyerene, divinylbenzene and methylmethacrylate, in the presence of surfactants of hydrophilic nature and an initiator. The choice of the surfactant composition and concentration, as well as other parameters of the reaction, such as initiator type, monomer concentration, governs the distribution of the microspheres diameters. Furthermore, the inventors have found that the quality of the coatings to be crated on the microspheres is also affected by two of these factors, namely, by the surfactant composition and by the initiator. As said, proper surfactants for coating purposes are of hydrophilic nature. Furthermore, it has been surprisingly found that the composition of the surfactants may serve as a tool for controlling the coating quality, by choosing proper fractions for the hydrophilic and hydrophobic surfactants.

By the term "surfactant" is meant to indicate a high molecular weight compound having one or more hydrophilic region(s) and one or more hydrophobic region(s). Illustrative and non limitative examples of suitable surfactants are polyethylene oxide, polyacrylic acid, copolymers of polyvinyl pyrrolidone-polyvinyl acetate in different ratios.

According to a preferred embodiment of the invention, the hydrophilic surfactant is chosen from among polyvinylpyrrolidone, polyacrylic acid and polyethyleneoxide. A preferred initiator is benzoylperoxide.

According to the invention, the microspheres which comprise surfactants on their surface, are treated in an organic solution, i.e. alcoholic solution, which includes alkyl silicates as an agent for the silica production, and a catalyst. Preferably, the alcoholic solution is composed of ethanol and water, the alkyl silicate is $Si(OEt)_4$ and the catalyst is ammonia.

Another purpose of the present invention is to provide a process for the preparation of hollow silica microspheres. According to the invention, these hollow shells are obtained by removing the inner polymeric core of the microspheres by burning or dissolving it. In particular, the burning off is performed by subjecting the microspheres to temperatures in the range of 400° C.–900° C. Alternatively, the dissolution is carried out by means of appropriate solvents. Illustrative, but non limitative, solvents comprise toluene, dimethylformamide, and the like.

According to the present invention, the polymeric microspheres, containing proper surfactants on their surface, may further be intermediately coated by a magnetic layer. In particular, said magnetic layer may be of $Fe_3O_4$. This coating process is carried out in an aqueous solution, in a temperature range of 55° C.–90° C., and in a pH range of 8 to 11, preferably between 10–11, since it was found that the magnetic intensity of the coated microspheres is enhanced if more basic conditions are applied. The ferrite formation involves oxidizing part of the $Fe^{+2}$ to $Fe^{+3}$, and then interaction between these two species to obtain the ferrite. The source for the divalent cation may be, for example, salts such as $FeCl_2.4H_2O$, and the oxidation reagent may be chosen, for instance, from among $NaNO_2$, $H_2O_2$ or air. The inventors have found that the magnetic properties of the coated microsphere are determined by the nature of the surfactant adsorbed initially on the particle surface. If hydrophobic surfactants are used, in combination with a hydrophilic one, a significant retardness is observed in the magnetic intensity of these coated microspheres, compared with those obtained with hydrophilic surfactant alone.

A further object of the present invention is to provide a process for the preparation of solid or hollow microspheres optionally comprising magnetic coatings, and further enveloped by silica layers. These coated microspheres are then subjected to further modification which have extremely important uses. The silica functionalizes in two different levels: it provides a defensive shell to the ferrite coating, and it serves as a source of optional covalent bonds, through which desired ligand may be attached to the system, in order to form the final, desired particle. According to said process, silica coating of said microspheres (which are optionally magnetic) is performed as hereinbefore described. Then, to a suspension of coated microspheres, which, as said, may be solid or hollow, appropriate ligands are added, comprising a functional group at their co -position. In particular, these ligands can form covalent bonds with the silica coating. The ligands may be chosen from among alkylsilane and/or alkylhydroxyl compounds, in particular $SiCl_3(CH_2)_nX$, $Si(OR)_3(CH_2)_nX$, $OH(CH_2)_nX$, wherein R is an alkyl substituent, n is between 2 to 20 and X is —$NH_2$, —$CH_3$, —$CO_2R$, —CN, etc. Of particular importance is the amine group, or other functional groups which can be converted to an amine group, because covalent binding of polyaldehyde ligands onto these groups may be further applied. The polyaldehyde derivatized microsphere surface obtained may be now coupled to biomaterials such as proteins. According to a preferred embodiment of the invention, in order to increase the interactions of said polyaldehyde ligands with the desired biomaterials, the residual ω-amine groups can be blocked by a proper reagent, for instance, acetic acid N-hydroxysuccin-imide ester. Furthermore, the inventors have found that acidic pH conditions improve the content of said aldehyde in the derivatized microsphere.

These solid and/or hollow aldehyde derivatized microspheres may now functionalize in several biological applications, when conjugated to biomaterials.

Figure 6:
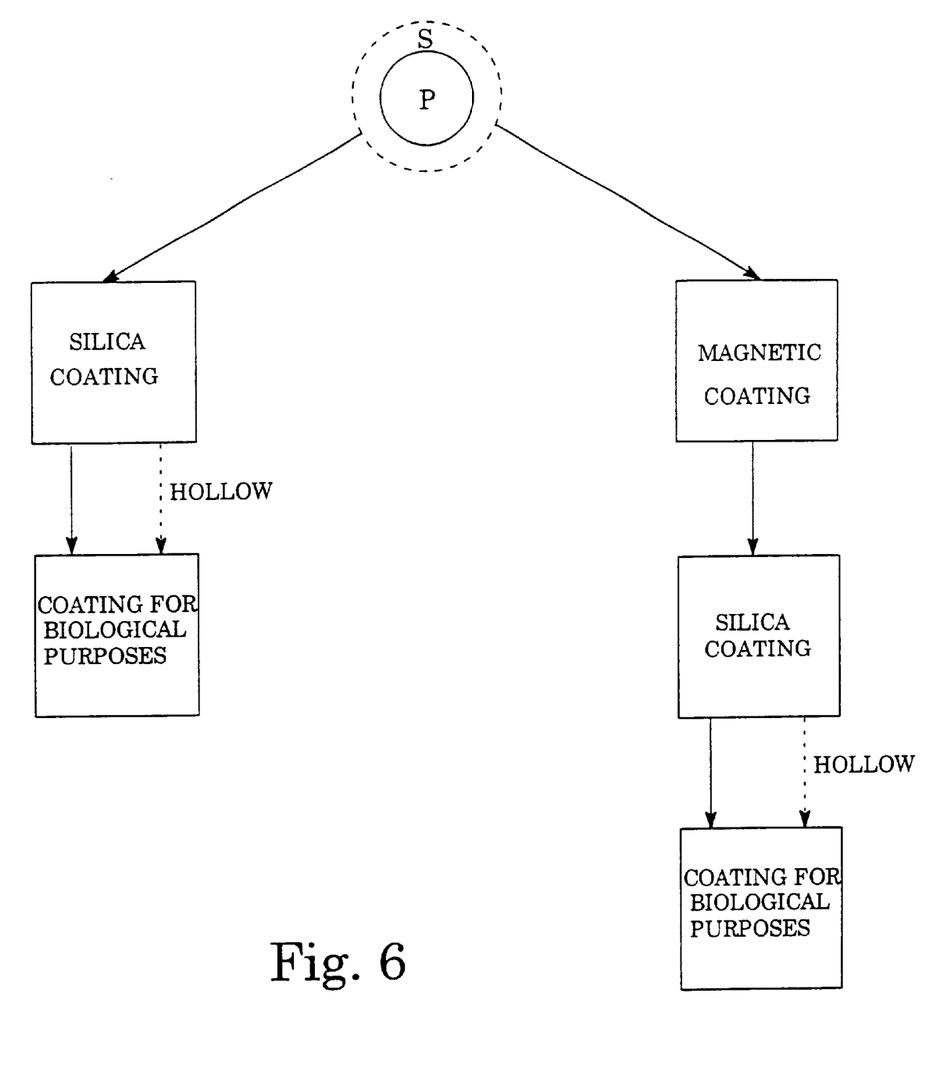
FIG. 6 summarizes various preferred embodiments of the present invention, wherein P is the polymeric microsphere and S is the surfactant adsorbed on its surface.

FIG. 6 summarizes various preferred embodiments of the present invention, wherein P is the polymeric microsphere and S is the surfactant adsorbed on its surface.

All the above and other characteristics and advantages of the invention will be better understood through the following illustrative and non-limitative description of preferred embodiments thereof.

BRIEF DESCRIPTION OF THE DRAWINGS

In the drawings:

FIGS. 3 (A and B) are cross-section pictures obtained by TEM of hollow silica microspheres prepared from polystyrene microspheres of ca. 1.8 μm average diameter coated with three layers of silica nanoparticles of ca. 30 nm average diameter;

DETAILED DESCRIPTION OF PREFERRED EMBODIMENTS

Experimental

Synthesis of polystyrene microspheres.

Figure 1:
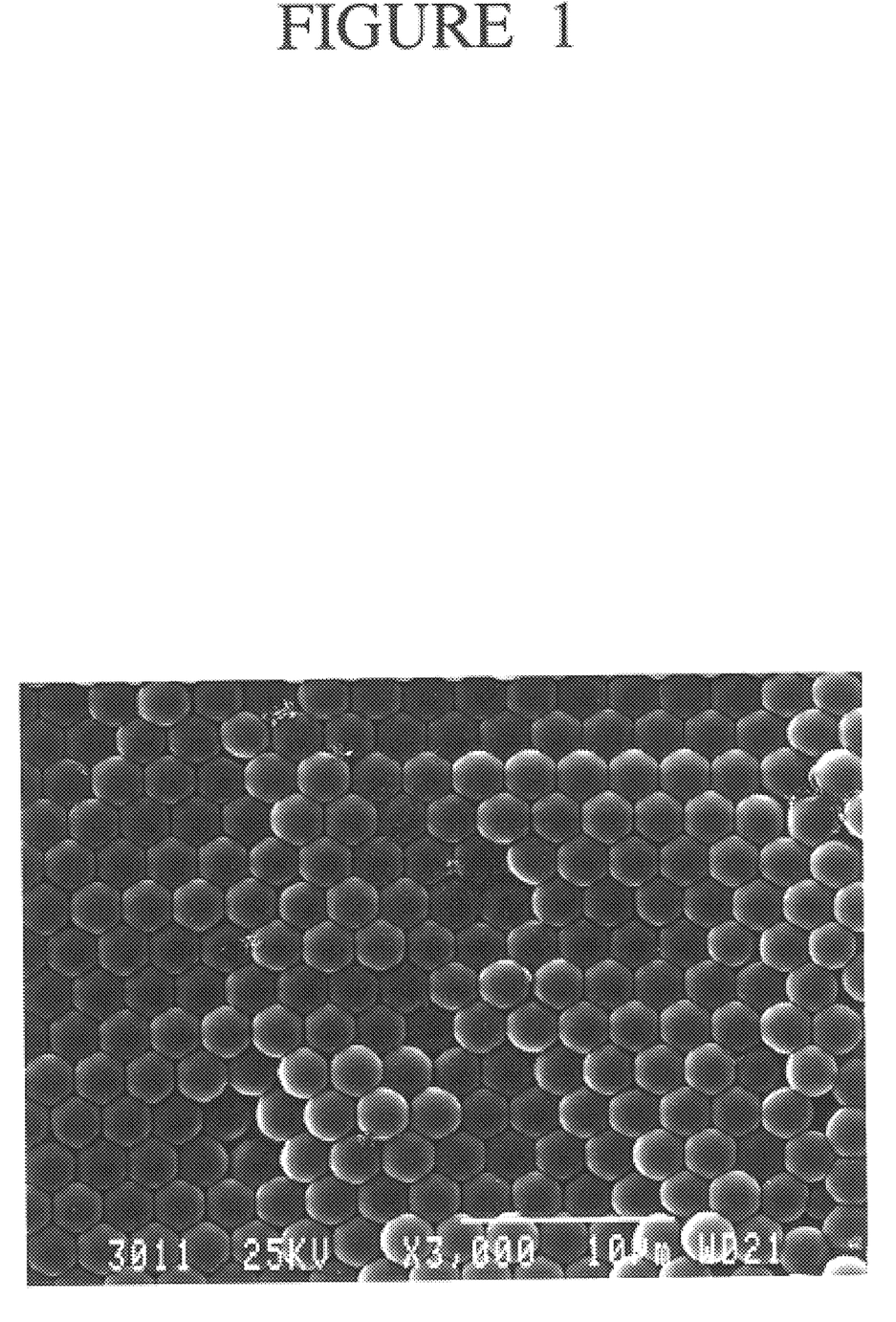
FIG. 1 is a SEM photograph of polystyrene microspheres.

Polystyrene microspheres were prepared according to the literature/C. K. Ober, K. P. Lok and M. L. Hair, J. of Polymer Sci., Polymer Letters Edition 23, 103 (1985)/. Briefly, These microspheres were prepared in a three-neck round-bottom flask equipped with a condenser. The flask was immersed in a constant temperature silicone oil bath at a preset temperature. In a typical reaction, A solution containing PVP (M.W. 360,000, 3.75 g) dissolved in ethanol (156 ml) and methyl cellosove (2-methoxyethanol, 62.5 ml) at room temperature was placed into the reaction flask and mechanically stirred (ca. 200 rpm). The temperature was then preset to 73° C. Nitrogen was bubbled through the solution for ca. 15 min. to exclude air, then a blanket of nitrogen was maintained over the solution during the polymerization period. A deairated solution containing benzoyl peroxide (1.5 g) and styrene (37.5 ml), previously purified through alumina column, was then added to the reaction flask. The polymerization reaction continued for 24 h. and then stopped by cooling. The obtained microspheres were washed by extensive centrifugation cycles with ethanol and then with water. The particles were then dried by lyophilization. Scanning Electron Microscopy (SEM) photomicrographs demonstrated the formation of monodispersed particles of 2.3 $\mu$m average diameter with a standard deviation of ca. 5% (FIG. 1).

The diameter of the formed microspheres were controlled by changing conditions, such as surfactant type, surfactant concentration, initiator type, monomer concentration, reaction time, etc. Thereby, monodispersed and polydispersed microsphere systems in sizes ranging from approximately 0.2 $\mu$m up to several microns were formed. For example, similar polymerization procedure as described above, substituting the initiator benzoyl peroxide with azobisisobutyronitrile, resulted in the formation of polydispersed microspheres with 4.2 $\mu$m average diameter instead of monodispersed microspheres of 2.3 $\mu$m average diameter obtained when benzoyl peroxide was used.

Crosslinked polystyrene microspheres of about 0.3 $\mu$m diameter were synthesized by a procedure similar to the procedure described above, substituting styrene with divinylbenzene or substituting styrene with a monomer mixture composed of 45% styrene and 55% divinylbenzene. Microns sized polydispersed crosslinked polystyrene microspheres were prepared by a suspension polymerization process, through a procedure similar to that described in the Q. C. Wang, F. Svec and M. J. Frechet, Polymer Bulletin 28, 569 (1992).

Synthesis of polychloromethylstyrene microspheres.

Monodispersed polychloromethylstyrene microspheres were prepared by a procedure similar to that described for polystyrene microspheres, substituting the solvent mixture (ethanol+methyl cellosove) with ethanol. In a typical reaction, 5.0 ml chloromethylstyrene were polymerized in 100 ml ethanol solution containing 1.15 g PVP (M.W. 360,000) and 100 mg azobisisobutironitrile. Thereby, monodispersed polychloromethylstyrene microspheres of ca. 1.2 $\mu$m diameter (standard deviation of ca. 5%) were formed. Microspheres with a variety of diameters were formed by changing conditions, such as monomer concentration, surfactant concentration, etc.

Synthesis of Polymethylmethacrylate Microspheres. Monodispersed polymethylmethacrylate (PMMA) microspheres were prepared by a procedure similar to that described for polystyrene microspheres, substituting the solvent mixture (ethanol+methyl cellosove) with ethanol. In a typical reaction, 23 ml methylmethacrylate were polymerized in 212 ml ethanol solution containing 3.75 g PVP (M.W. 360,000) and 1.5 g bezoylperoxide. Thereby, PMMA microspheres of ca. 2.0 $\mu$m diameter were formed. Microspheres with a variety of diameters were formed by changing conditions, such as monomer concentration, surfactant concentration, etc.

Synthesis of silica nanoparticles.

Silica nanoparticles were prepared by the sol-gel technique by polymerization of $Si(OEt)_4$ according to the Stober Method/W. Stober, A. Fink and E. Bohn, J. Colloid Interface Sci. 26, 62 (1968). Briefly, particles of 30 nm average diameter were prepared by adding into a flask according to the listed order the following reagents: ethanol (93.6 ml), distilled water (1.9 ml), ammonium hydroxide (1.3 ml) and $Si(OEt)_4$ (3.2 ml). The resulting solution was then shaken at room temperature for ca. 12 h. The formed nanoparticles were washed by evaporation of the unreacted monomer, ethanol and ammonia. Water was added during the evaporation to retain the total volume of the silica suspension. Thereafter, water was evaporated up to ca. 10 ml total volume. This suspension was then dried in a vacuum oven. Particle analyzer measurements demonstrated the formation of silica nanoparticles of ca. 30 nm average diameter. Silica nanoparticles of different sizes were prepared by changing conditions, such as monomer concentration, water concentration, etc.

Synthesis of Polyacrolein Nanoparticles.

Polyacrolein nanoparticles were synthesized according to the literatures. Margel, Reactive Polymers 1, 241 (1983). Briefly, polyacrolein nanoparticles of ca. 70 nm average diameter were prepared by cobalt irradiation (approx. 1 Mrad) of a deairated solution containing 90 ml distilled water, 1 g sodium dodecyl sulfate and 10 ml acrolein. The formed microspheres were then washed by extensive dialysis against distilled water.

EXAMPLE 1

Preparation of thin coatings from silica nanoparticles on polystyrene microspheres.

Dried polystyrene microspheres of 1.8 pm average diameter containing polyvinylpyrrolidone adsorbed on its surfaces, prepared according to the description in the experimental part, were added into a flask containing ethanol (93.6 ml) and distilled water (1.9 ml). The microspheres were then suspended in the solvent by sonication. Ammonium hydroxide (1.3 ml) and $Si(OEt)_4$ (3.2 ml) were then added to the previous polystyrene suspension. The resulting suspension was then shaken at room temperature for about 12 h. The formed thin coated silica nanoparticles-polystyrene microspheres were washed with water from non-grafted silica nanoparticles (ca. 30 nm average diameter) by repeated centrifugation cycles at ca. 3000 rpm for ca. 40 min. The silica-coated polystyrene microspheres were then dried in a vacuum oven. A second coating cycle was performed similarly, substituting the polystyrene microspheres with the silica-coated polystyrene microspheres. A similar procedure was performed for a third, fourth, etc. coating cycles.

Figure 2:
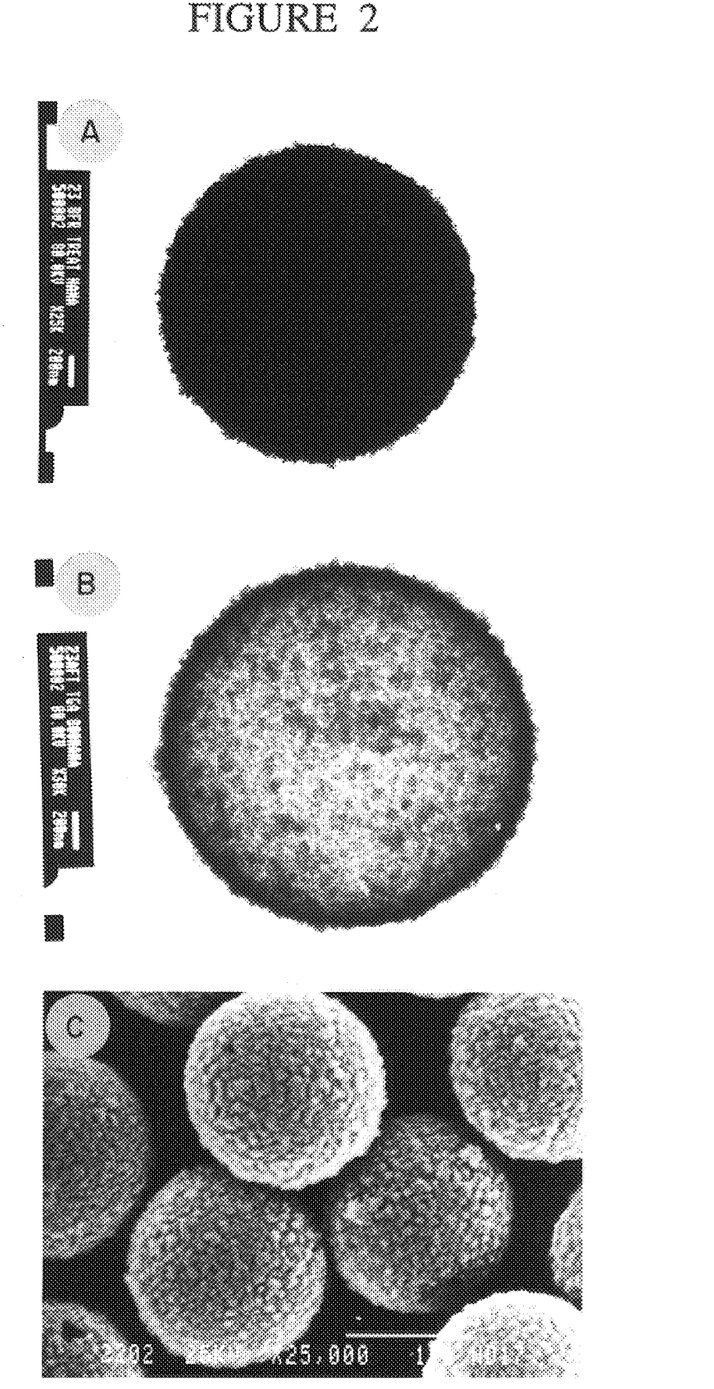
FIG. 2A is a TEM picture of a polystyrene microsphere of ca. 1.8 pm coated with three layers of silica nanoparticles of ca. 30 nm average diameter.
FIGS. 2B and 2C are TEM and SEM pictures, respectively of hollow microspheres obtained by burning off the organic content of these coated microspheres at 800° C. for 12 h.

FIG. 2A illustrates a TEM photomicrograph of polystyrene microsphere coated with three layers of silica monoparticles.

Figure 3:
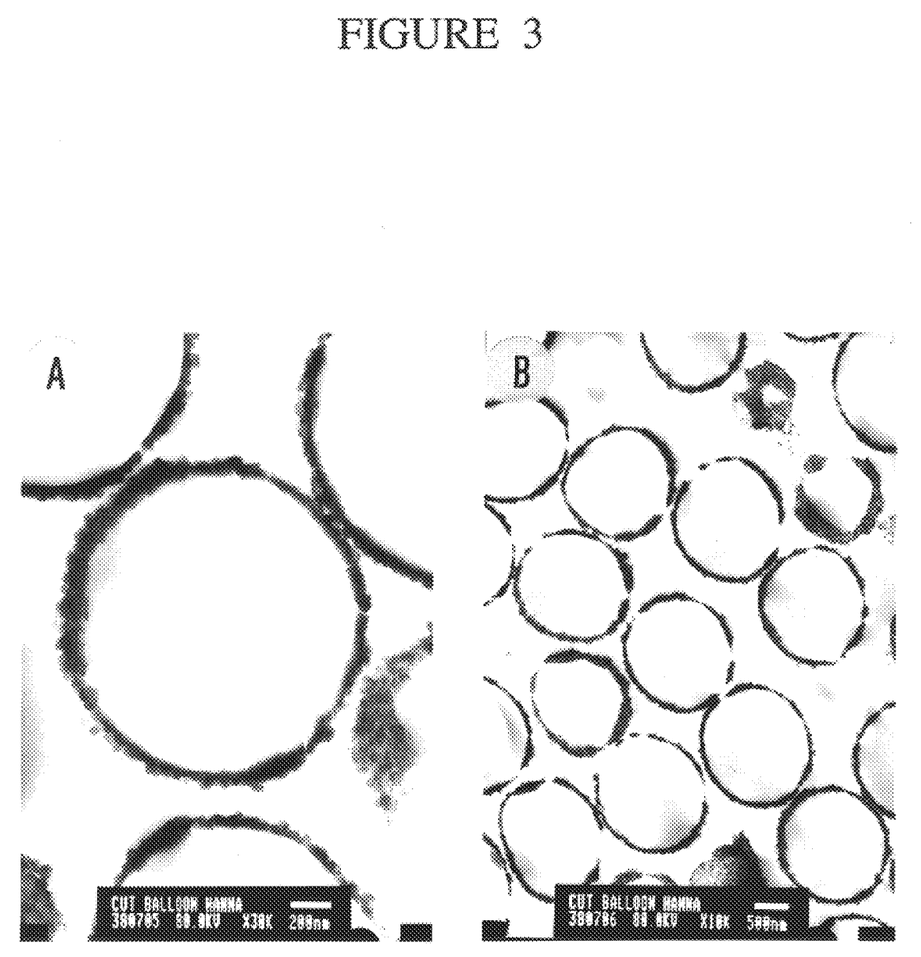

Cross section photomicrographs of the thin coated polystyrene microspheres taken with transmission electron microscopy (TEM) [FIG. 3] demonstrated that the thickness of each layer of the continuous silica nanoparticle coatings is about 25–30 nm. Thermogravimetric studies and/or elemental analysis measurements demonstrated that the percent silica in the first coating is about 7.8%, in the second about 13.5%, in the third about 18.5% and in the fourth about 20.5%.

EXAMPLE 2

Example 1 was repeated, substituting the 3.2 ml $Si(OEt)_4$ with 1.8 ml $Si(OEt)_4$. Similar results were obtained, except that the silica nanoparticle coating on the polystyrene microspheres decreased from about 30 nm average diameter to about 20 nm average diameter.

EXAMPLE 3

Preparation of continuous thin coatings of silica nanoparticles on polystyrene microspheres.

Dried polystyrene microspheres of about 1.8 μm average diameter containing polyvinylpyrrolidone adsorbed on its surfaces, prepared according to the description in the experimental part, were added into a flask containing ethanol (93.6 ml) and distilled water (1.9 ml). The microspheres were then suspended in the solvent by sonication. Ammonium hydroxide (1.3 ml) and $Si(OEt)_4$ (3.2 ml) were then added to the previous polystyrene suspension. The resulting suspension was then shaken at room temperature for ca. 12 h. A second layer of silica coating was then prepared by adding to the suspension 0.6 ml distilled water and 3.2 ml $Si(OEt)_4$. The reaction was then continued for additional about 5 h. The formed silica coated polystyrene microspheres were then washed according to the description in Example 1. The percent silica obtained for the first and second coatings of the polystyrene was similar to that obtained in Example 1. A third continuous silica coating on polystyrene microspheres was difficult to prepare because of the difficulties existed in separation of grafted silica nanoparticles from ungrafted silica nanoparticles.

EXAMPLE 4

Preparation of thin coatings from silica nanoparticles on polystyrene microspheres of different diameters.

Examples 1–3 were repeated substituting the polystyrene microspheres of about 1.8 μm average diameter adsorbed with PVP on its surfaces with similar type microspheres, crosslinked and not crosslinked, with variety of diameters, i.e. about 0.3, 2.3, 5.2 and 8.0 μm average diameter. Cross section photomicrographs demonstrated similar silica coatings as that obtained in Examples 1–3.

EXAMPLE 5

Examples 1–4 were repeated substituting polystyrene microspheres containing PVP adsorbed on its surfaces with polystyrene microspheres containing other hydrophilic surfactants adsorbed on its surfaces, i.e. polyacrylic acid and polyethyleneoxide. Cross section photomicrographs demonstrated similar silica coatings as that obtained in Examples 1–4.

EXAMPLE 6

Effect of hydrophobic surfactants adsorbed on the polystyrene microspheres on the thin coatings from silica nanoparticles.

Examples 1, 3 and 4 were repeated substituting polystyrene microspheres containing PVP adsorbed on its surfaces with polystyrene microspheres containing surfactants with decreased order of hydrophilic/hydrophobic ratio on its surfaces, i.e. PVP, PVP-PVAc (60:40) and PVAc. Elemental analysis measurements showed that the percent silica significantly decreased when the hydrophilic/hydrophobic ratio of the adsorbed surfactants decreased. For example, the percent silica measured for the first silica coating on polystyrene microspheres prepared with benzoylperoxide was ca. 7.8%, 3.7% and 0.5% for microspheres adsorbed on its surfaces with PVP, PVP-PVAc (60:40) and PVAc, respectively.

EXAMPLE 7

Example 6 was repeated with polystyrene microspheres prepared with the initiator azobisisobutironitrile instead of benzoylperoxide. Thereby, The hydrophobic character of the formed microspheres increased relative to the microspheres prepared with benzoylperoxide. Thermogravimetric measurements also clearly demonstrated that the percent silica coated on the polystyrene significantly decreased when the hydrophilic/hydrophobic ratio of the adsorbed surfactants decreased. For example, the percent silica measured for the first silica coating on polystyrene microspheres prepared with azobisisobutironitrile was about 6.4%, 0.4% and 0.0% for microspheres adsorbed on its surfaces with PVP, PVP-PVAc (60:40) and PVAc, respectively. Similar behavior was also observed for the second silica coating on polystyrene microspheres prepared with azobisisobutironitrile, i.e. the percent silica after the second coating was about 8.8%, 2.0% and 1.0% for microspheres adsorbed on its surfaces with PVP, PVP-PVAc (60:40) and PVAc, respectively.

EXAMPLE 8

Preparation of thin coatings from silica nanoparticles on polychloromethylstyrene microspheres and/or polymethylmethacrylate microspheres.

Examples 1–7 were repeated, substituting the polystyrene microspheres with polychloromethylstyrene microspheres and/or polymethylmethacrylate microspheres prepared according to the description in the experimental part. Cross section photomicrographs indicated similar results.

EXAMPLE 9

Preparation of hollow silica microspheres.

Hollow silica microspheres were prepared by burning off (i.e. ca. 400° C. or above) the organic core of polystyrene microspheres coated with silica nanoparticles, prepared according to Examples 1–5.

FIG. 2A is a TEM picture of a polystyrene microsphere of ca. 1.8 μm coated with three layers of silica nanoparticles of ca. 30 nm average diameter. FIGS. 2B and 2C are TEM and SEM pictures, respectively of hollow microspheres obtained by burning off the organic content of these coated microspheres at 800° C. for 12 h. Infrared measurements indicated the total removal of the organic core from the silica shell.

FIGS. 3 (A and B) are cross-section pictures obtained by TEM of hollow silica microspheres prepared from polystyrene microspheres of ca. 1.8 μm average diameter coated with three layers of silica nanoparticles of ca. 30 nm average diameter.

Figure 4:
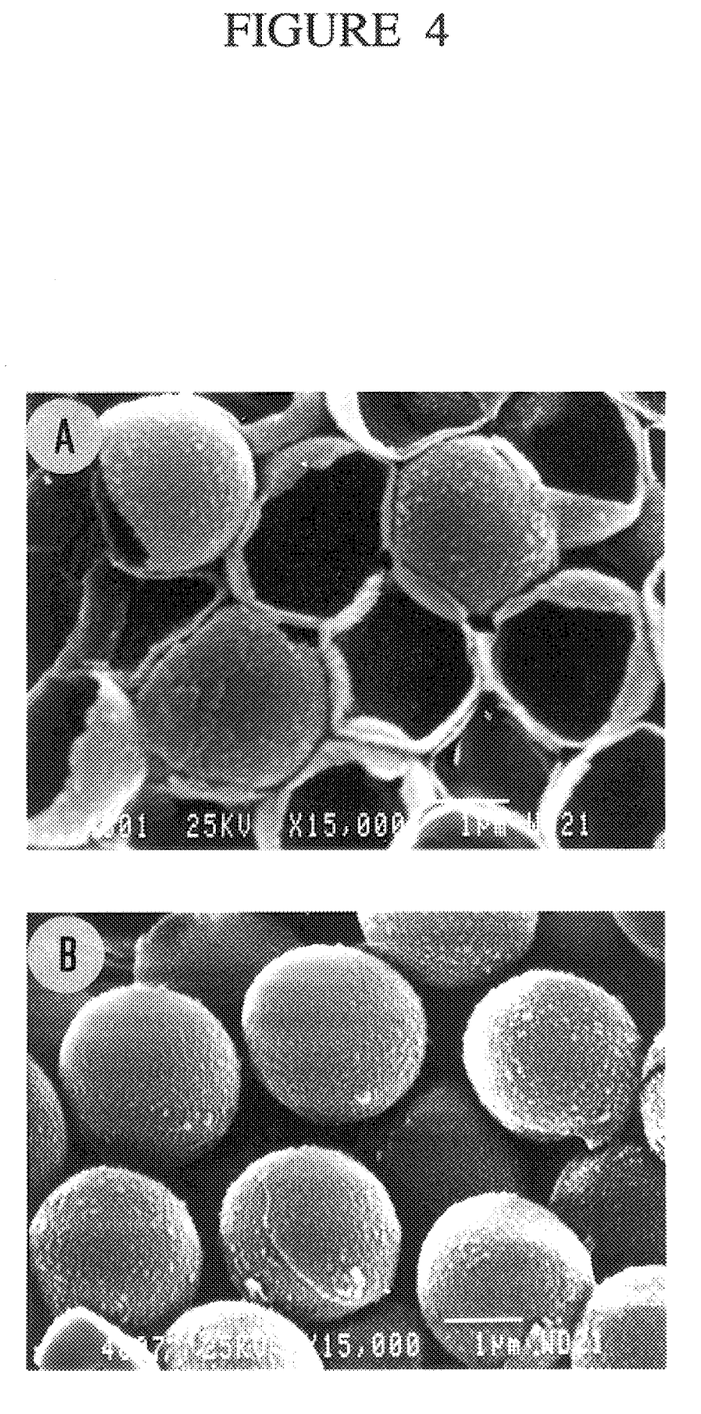
FIG. 4 shows SEM pictures of hollow silica microspheres obtained by burning off the organic core of polystyrene microspheres of ca. 2.3 μm coated with a single layer of silica nanoparticles of ca. 30 nm diameter (FIG. 4A), and three layers of similar silica nanoparticles (FIG. 4B)

FIG. 4 shows SEM pictures of hollow silica microspheres obtained by burning off the organic core of polystyrene microspheres of ca. 2.3 μm coated with a single layer of silica nanoparticles of ca. 30 nm diameter (FIG. 4A) and three layers of similar silica nanoparticles (FIG. 4B). The hollow silica microspheres composed of three layers of silica nanoparticles are stable while the hollow silica microspheres composed of a single silica nanoparticles layer are mostly broken. These observation may due to the instability of the coating composed of a single silica layer to stand the vacuum applied for the SEM use.

EXAMPLE 10

Hollow silica microspheres were also prepared by dissolving with appropriate solvents (e.g. toluene, dimethylformamide, etc.) the organic core of polystyrene microspheres coated with silica nanoparticles, prepared according to Examples 1–5. The hollow microspheres obtained in this way usually contained, except silica, also traces of organic polymers which could not be removed by this process.

EXAMPLE 11

Efforts to prepare hollow silica microspheres by using the procedures described in Examples 9 and 10 with polystyrene microspheres containing PVAc adsorbed on its surfaces and coated with a single layer and/or two layers of silica nanoparticles prepared according to examples 6 and 7 failed, due to the insignificant silica coating on these microspheres.

EXAMPLE 12

Examples 9–11 we re repeated substituting polystyrene microspheres with polychloromethylstyrene microspheres or/and polymethylmethacrylate microspheres coated with silica nanoparticles prepared according to Example 8. Similar results were obtained.

EXAMPLE 13

Preparation of magnetic thin coating from $Fe_3O_4$ on polystyrene microspheres.

The coating was performed in a six-neck round-bottom flask. One neck in the center was used for mechanical stirring, two other necks were used for purging nitrogen and for the exit of this gas, the other three necks were used for gradual introducing into the flask, during the coating process, deairated aqueous solutions from iron chloride, sodium nitrite and sodium hydroxide, respectively. The flask was immersed in a constant temperature silicone oil bath at a preset temperature. In a typical reaction, An aqueous suspension (200 ml) containing 10 g polystyrene microspheres of ca. 2.3 µm average diameter with PVP adsorbed on its surfaces (prepared according to the description in the experimental part) was sonicated to dispersed the particles, placed then into the reaction flask and mechanically stirred (ca. 200 rpm). The temperature was then preset to 60° C. Nitrogen was bubbled through the suspension during the coating process to exclude air. 1 ml of the iron chloride tetrahydrate aqueous solution (12 mmol in 100 ml $H_2O$) and 1 ml of sodium nitrite aqueous solution (0.2 mmol in 100 ml $H_2O$) were then successively introduced into the reaction flask. Thereafter, sodium hydroxide aqueous solution (5 mmol in 100 ml $H_2O$) was added until pH of ca. 10 was reached. This procedure was repeated 40 times. During this coating process the microspheres became brown-black colored. The magnetic suspension was then cooled to room temperature. The formed magnetic polystyrene microspheres were then washed extensively in water with a magnet and dried then with a lyophilizer.

Figure 5:
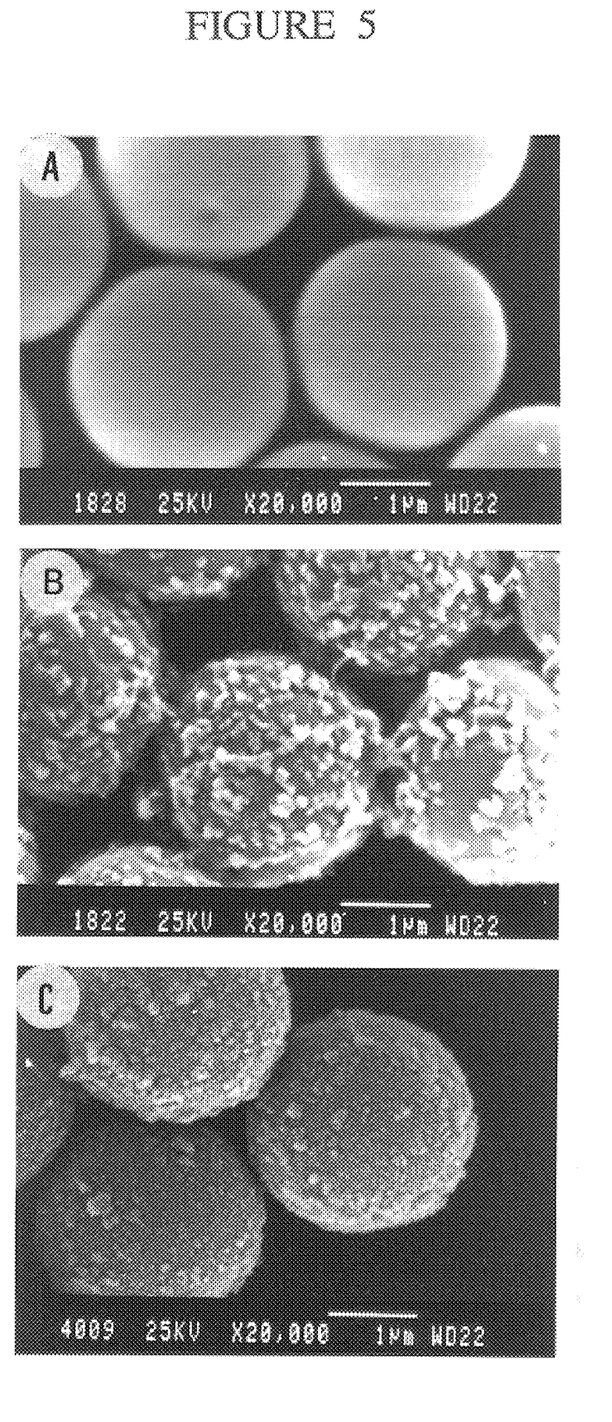
FIG. 5A illustrates SEM photomicrograph of polystyrene microsphere of ca. 2.3 μm diameter.
FIG. 5B Illustrates the magnetic coating on polystyrene microspheres of ca. 2.3 μm diameter.
FIG. 5C illustrates the first silica nanoparticles coating on magnetic polystyrene microspheres of about 2.3 μm, prepared according to example 13.

FIG. 5A illustrates SEM photomicrograph of polystyrene microspheres of about 2.3 µm.

FIG. 5B illustrates that the iron oxide coating on these polystyrene microspheres is in islands and not continuous. Thermogravimetric measurements shows that the percent iron oxide coating on the microspheres is approximately between 6%–8%.

EXAMPLE 14

Example 13 was repeated under a variety of conditions: (a) Temperature range between 55° C. to 90° C., similar results were obtained; (1) pH range between 8 to 11, the magnetic intensity of the coated microspheres prepared at pH range between 10 to 11 was higher than that prepared at the lower pH range; (c) Mole ratio $[NaNO_2]/[FeCl_2.4H_2O]$ up to 10 times higher than that described in the previous example, similar results were obtained; (d) Addition to the microspheres suspension up to five times more of the different reagents ($NaNO_2$, $FeCl_2.4H_2O$, and NaOH) causes to the corresponding growth of the iron oxide coating on the microspheres.

EXAMPLE 15

Experiments 13 and 14 were repeated, substituting the oxidizing agent $NaNO_2$ with other oxidizing agents, i.e. $H_2O_2$ and air. Similar results were obtained.

EXAMPLE 16

Examples 13–15 were repeated, substituting the polystyrene microspheres of about 2.3 µm containing PVP adsorbed on its surfaces with microspheres of different sizes, i.e. about 0.3, 1.8 and 6.0 µm containing different hydrophilic surfactants adsorbed on its surfaces, i.e. PVP, polyacrylic acid and polyethyleneoxide. Similar results were obtained (percent iron oxide between 6%–10%.)

EXAMPLE 17

Examples 13–15 were repeated, substituting the polystyrene microspheres of ca. 2.3 µm containing PVP adsorbed on its surfaces with microspheres containing hydrophobic surfactants, such as PVAc. The percent iron oxide of these coated microspheres was significantly lower (i.e. ca. 3%) than that adsorbed with hydrophilic surfactants. These observations also lead to a significant lower magnetic intensity of these coated microspheres relative to the microspheres that contained hydrophilic surfactants adsorbed on its surfaces.

EXAMPLE 18

Preparation of magnetic thin coatings from $Fe_3O_4$ on polychloromethylstyrene microspheres and/or polymethylmethacrylate microspheres.

Examples 13–17 were repeated, substituting polystyrene microspheres with polychloromethylstyrene microspheres and/or polymethylmethacrylate microspheres prepared as described in the experimental section hereof. Similar results were obtained.

EXAMPLE 19

Preparation of thin coating from silica on magnetic polystyrene microspheres.

Examples 1–7 were repeated substituting the polystyrene microspheres with polystyrene microspheres thin coated with $Fe_3O_4$, prepared according to the description in Examples 13–17. Similar results were obtained. FIG. 5C, for example, illustrates the first silica nanoparticles coating on magnetic polystyrene microspheres of ca. 2.3 µm, prepared according to example 13. The process described above was also repeated with coatings prepared from silica nanoparticles of sizes ranging from ca. 20 nm up to ca. 0.1 µm. The separation of grafted silica nanoparticles from non-grafted was performed with a magnetic field. SEM and TEM photomicrographs demonstrated the complete coating of the microsphere surfaces with silica nanoparticles.

EXAMPLE 20

Preparation of thin coatings from silica on magnetic polychloromethylstyrene microspheres and/or polymethylmethacrylate microspheres.

Example 8 was repeated substituting the polychloromethylstyrene microspheres and/or polymethylmethacrylate microspheres with similar microspheres thin coated with $Fe_3O_4$ prepared according to the description in experiment 18. Similar results were obtained.

EXAMPLE 21

Preparation of magnetic hollow silica microspheres.

Examples 9–12 were repeated, substituting the polystyrene microspheres and/or polychloromethylstyrene microspheres and/or polymethylmethacrylate microspheres coated with silica nanoparticles with similar microspheres coated with $Fe_3O_4$ and with silica, prepared according to the description in Examples 19 and 20. Similar results were obtained.

EXAMPLE 22

Hydrophilic/hydrophobic character of the hollow microspheres.

Silica hollow microspheres and/or magnetic silica hollow microspheres prepared by burning off the organic core from the inorganic shell at temperatures above ca. 900° C. were floated on water due to its hydrophobic character. On the other hand, similar hollow microspheres prepared below ca. 600° C. sank in water. However, if these dried hollow microspheres are reburned at temperatures above ca. 900° C. they also become hydrophobic and float on water.

EXAMPLE 23

Surface modification of the silica coated microspheres and/or silica hollow microspheres.

Derivatization of the previous described solid and hollow silica microspheres through its hydroxyl groups with ω-functionalized alkylsilane compounds and/or ω-functionalized alkylhydroxyl compounds has been performed by the following general procedure: Dried microspheres were added to the appropriate solvent. The resulting mixture was then sonicated in order to dispersed the particles in the solvent. The derivatization of the suspended microspheres was then accomplished at the desired temperature for the desired period of time by adding the appropriate ω-functionalized alkylsilane compound and/or ω-functionalized alkylhydroxyl compound to the microspheres suspension. The derivatized microspheres were then washed from undesired compounds by repeated centrifugation cycles under appropriate conditions (or with a magnetic field if magnetic microspheres were used). The washed derivatized microspheres were then dried with a lyophilizer and/or a vacuum oven. If necessary, in order to prevent nonspecific interactions with the silica (due to its negative charge) blocking of residual silica with appropriate reagents, such as bovine serum albumin (BSA), was performed by suspending the derivatized microspheres in phosphate buffered saline (PBS) solution containing 1% BSA for ca. 2 h at room temperature. The derivatized microspheres were then washed by centrifugation (or with a magnetic field if magnetic microspheres were used) with distilled water and then dried by lyophilization.

For example, the following typical derivatization procedures are hereby briefly described:

1. Derivatization of silica microspheres in aqueous solution with alkylsilane compounds, i.e. $Si(OEt)_3(CH_2)_3NH_2$.

In a typical experiment, 1 g of dried polystyrene microspheres (ca. 2.3 μm diameter) coated twice with silica nanoparticles were introduced into a three neck flask containing 800 ml buffer acetate, 0.1 M at pH 5.5. The mixture was sonicated for dispersing the particles. 8 ml of the amphiphile $Si(OEt)_3(CH_2)_3NH_2$ were then added to the suspended microspheres. The suspension was then mechanically stirred at 60° C. for 18 h. Thereafter, the derivatized microspheres were washed by two centrifugation cycles in buffer acetate and another two centrifugation cycles in distilled water. The ω-amino derivatized microsphere surfaces were then dried by lyophilization. If necessary, albumin blocking of the derivatized microspheres was then performed as described previously.

2. Derivatization of silica microspheres in organic solution with alkylsilane compounds, i.e. $Si(OEt)_3(CH_2)_2CN$ and/or $SiCl_3(CH_2)_{17}CH_3$.

In a typical experiment, 1 g of dried crosslinked polystyrene microspheres (ca. 0.3 μm diameter) coated twice with silica nanoparticles were introduced into a three neck flask containing 100 ml bicyclohexyl (or toluene). The mixture was sonicated for dispersing the particles. 1 ml of the amphiphile $Si(OEt)_3(CH_2)_2CN$ or $SiCl_3(CH_2)_{17}CH_3$ was then added to the suspended microspheres. The suspension was then mechanically stirred at room temperature (or at 110° C. when toluene used) for ca. 5 h. Thereafter, the derivatized microspheres were washed by two centrifugation cycles with bicyclohexyl (or toluene) and another two centrifugation cycles with acetone. The derivatized microsphere surfaces were then dried by lyophilization. The reduction of the ω-nitrile microsphere surfaces to ω-amine derivatized surfaces was accomplished by suspending the derivatized microspheres at 50° C. for ca. 18 h in a THF solution containing 1 M diborane. The reduced surfaces were then washed by centrifugation in THF and then in acetone. The primary amino derivatized microsphere surfaces were then dried by lyophilization. If necessary, albumin blocking of the derivatized microspheres was then performed as described previously.

3. Derivatization of silica microspheres in organic solution with alkylhydroxyl compounds, i.e. $OH(CH_2)_7CH_3$.

In a typical experiment, 1 g of dried crosslinked polystyrene microspheres (ca. 0.3 μm diameter) coated twice with silica nanoparticles were introduced into a three neck flask containing 100 ml octanol. The mixture was sonicated for dispersing the particles. The suspension was then mechanically stirred at 15° C for ca. 5 h. Thereafter, the derivatized microspheres were washed by two centrifugation cycles with octanol and another two centrifugation cycles with acetone. The derivatized microsphere surfaces were then dried by lyophilization. If necessary, albumin blocking of the derivatized microspheres was then performed as described previously.

EXAMPLE 24

Covalent binding of polyaldehyde ligands onto the ω-amine derivatized microsphere surfaces.

In a typical experiment, the ω-amine derivatized microsphere surfaces prepared as described in example 23 were shaken at room temperature for approximately 5 h in an aqueous solution containing ca. 1% of the different polyaldehyde ligands, i.e. glutaraldehyde or polyacrolein nanoparticles of ca. 70 nm diameter prepared as described in the experimental part. The polyaldehyde derivatized microsphere surfaces were then washed by extensive centrifugation with distilled water. If necessary, in order to decrease nonspecific interactions with biomaterials, i.e. proteins, residual ω-amine groups of the polyaldehyde derivatized surfaces were blocked with acetic acid N-hydroxysuccinimide ester by repeated the procedure described for the covalent binding of the polyaldehyde ligands to the microsphere surfaces, substituting the polyaldehyde ligands with 0.2% acetic acid N-hydroxysuccin-imide ester in PBS solution. The blocked polyaldehyde derivatized microspheres were then washed as previously described. The washed derivatized microspheres were then dried by lyophilization.

EXAMPLE 25

Covalent binding of acrolein onto the ω-amine derivatized microsphere surfaces.

The ω-amine derivatized microsphere surfaces prepared as described in example 23 were shaken at room temperature for approximately 5 h in an aqueous solution, at pH range between 2–9, containing ca. 1% acrolein. The formed polyaldehyde derivatized microsphere surfaces were then washed by extensive centrifugation with distilled water. The polyaldehyde derivatized microspheres were then treated as described in example 24. Our studies demonstrated that the binding of acrolein at acidic pH, i.e. between pH-2 to pH-4 resulted in approximately 3 to 10 times more aldehyde content in the derivatized microspheres.

EXAMPLE 26

Coupling of amino ligands (i.e. proteins) to the polyaldehyde derivatized microsphere surfaces.

In general, the solid and/or hollow polyaldehyde derivatized microspheres were shaken at room temperature (or other desired temperature) for few hours with the desired protein in PBS (or other physiological solution). Unbound protein was then removed by centrifugation cycles (or by a magnetic separation) in PBS. Residual aldehyde groups were then blocked with amino ligands, such as BSA, hydroxylamine or ethanol amine in pH-7. The protein conjugated microspheres were kept in PBS (or water) at 4° C. or kept dried after lyophilization.

In a typical experiment, 10 mg microspheres composed of polyaldehyde derivatized silica coated polystyrene microspheres of ca. 1.8 $\mu$m diameter were shaken at room temperature for 4 h with 1 mg trypsin in 5 ml PBS. Unbound trypsin was then separated by 3 centrifugation cycles in PBS. Residual aldehyde groups on the microspheres were then blocked by shaking the conjugated microspheres at room temperature for 4 h with BSA (1%) in PBS. Unbound BSA was then removed by 2 centrifugation cycles in PBS and then 2 centrifugation cycles in distilled water. The trypsin conjugated microspheres were then dried by lyophilization.

By using similar procedure, the following proteins were covalently bound to the different polyaldehyde derivatized microspheres: goat anti-rabbit IgG (G$\alpha$RIgG), goat anti-mouse Ig (G$\alpha$MIg), protein A, trypsin and lysozyme.

EXAMPLE 27

Biological applications of the protein-conjugated polyaldehyde microspheres.

1. Diagnostics: Determination of $\alpha_1$-antitrypsin in human serum.

The activity of the trypsin conjugated microspheres prepared as described in example 26 was checked with the substrate $\alpha$-N-benzoyl-DL-arginine p-nitroanilide (BAPNA). The conjugated trypsin in reaction with BAPNA in Tris buffer (pH-8) liberated p-nitroaniline of which its absorbance value at 400 nm was measured.

The determination of $\alpha_1$-antitrypsin in human serum was based on the inhibitory effect of antitrypsin of serum on the hydrolysis of BAPNA by the conjugated trypsin in Tris buffer. The reaction is stopped by adding acetic acid, and the absorbance is then read at 400 nm. At this wavelength the liberated p-nitroaniline has a molar absorptivity of 10,500. Briefly, before the assay, each examined serum was diluted 1000 fold with Tris buffer. 2 ml of the diluted serum were then incubated at 37° C. for 30 min with 1 ml suspension containing 10 mg trypsin-conjugated microspheres in Tris buffer. 5 ml of BAPNA solution (prepared by dissolving 100 mg BAPNA in 2.3 ml dimethylsulfoxide, and then diluted 1 ml of this stock solution with 100 ml Tris buffer at pH 8.0) at 37° C. was then added for 30 min to the serum-trypsin-conjugated microspheres suspension. The reaction was stopped by adding 1 ml glacial acetic acid. The degree of interaction between the conjugated trypsin and BAPNA was then determined by the absorbance value at 400 nm. Control experiments were carried out with 4% HSA by using the same procedure. The precise amount of $\alpha_1$-antitrypsin was determined by comparison to a standard curve obtained from a known amount of $\alpha_1$-antitrypsin. The results obtained by this method were in a good agreement with the results obtained by the radial immunodiffusion method/A. A. Dietz, H. M. Rubinstein-and L. Hodges, Clin. Chem. 20 (3), 396 (1974); J. Travis and D. Johnson, Methods Enzymol. 80, 754 (1981)/, the common clinical method applied for determination of $\alpha_1$-antitrypsin in human serum.

2. Specific cell labeling of human red blood cells.

Fresh human red blood cells (HRBC) were shaken for 50 min at 4° C. with rabbit anti-HRBC ($10^6$ HRBC with 0.8 $\mu$g rabbit anti-HRBC) antibodies. The sensitized cells were separated and washed 4 times by centrifugation with PBS. The washed sensitized cells were then shaken at 4° C. for 1 h with G$\alpha$RIgG magnetic conjugated microspheres (5 mg) prepared as described in example 26. The labeled cells were then separated from excess microspheres by 3 centrifugations with PBS. Control experiments carried out similarly, substituting the sensitized rabbit anti-HRBC with non-sensitized HRBC. Examination with light microscopy demonstrated the specific labeling of the RBC by the G$\alpha$RIgG conjugated microspheres. The control cells, on the other hand, were not labeled at all.

3. Separation of turkey RBC from human RBC.

A mixture containing $10^6$ human RBC and $10^6$ turkey RBC was treated with magnetic microspheres by using the labeling procedure described in (2). A small magnet was then fitted on the outside wall of a vial containing 5 ml PBS suspension of the mixture of cells. After ca. 5 min, cells that were not attracted to the wall were isolated. The attracted cells were resuspended in PBS and the magnetic separation repeated twice. Examination in light microscopy demonstrated separation efficiency of 98%–100% of the human RBC from the turkey RBC.

4. Specific labeling of mouse splenocytes bearing surface immunoglobulins (B cells).

G$\alpha$MIg conjugated microspheres (5 mg) prepared as described in example 26 were shaken at 4° C. for 1 h with purified mouse splenocytes ($10^6$). The labeled cells were then separated from excess microspheres by 3 centrifugation cycles with PBS. Control experiments carried out similarly, substituting the mouse splenocytes with mouse thymocytes. Examination with light microscopy demonstrated the specific labeling of the mouse splenocytes with the G$\alpha$MIg conjugated microspheres. The control cells, on the other hand, were not labeled at all.

All the above description and examples have been provided for the purpose of illustration and are not intended to limit the invention in any way. Many modifications can be carried out in the process of the invention. For instance, different polymeric materials, coatings, solutions, initiators and conjugates can be used, to produce various full or hollow microspheres. Furthermore the microspheres of the invention can be used in a variety of applications, medical, diagnostics and others, all without exceeding the scope of the invention.

What is claimed is:

1. A process for the preparation of a microsphere comprising a coating composed of one or more silica nanoparticles layers, comprising the steps of
  a) providing a microsphere of polymeric material, the said microsphere having adsorbed on its surface one or more surfactants having a hydrophilic nature; and
  b) causing a layer of silica nanoparticles to coat the surface of the said microsphere by means of polymerization of alkyl silicates onto the surface of said microsphere.

2. A process according to claim 1, further comprising the step of coating the surface of the microsphere with one or more additional layers comprising magnetic material, before creating the silica coating.

3. A process according to claim 2, wherein the magnetic material is $Fe_3O_4$.

4. A process according to claim 3, wherein the magnetic coating of $Fe_3O_4$ is obtained by introducing the microspheres and $Fe^{+2}$ ions into an aqueous solution, in the presence of oxidizing agents.

5. A process according to claim 4, wherein the temperature of the solution is between 55° C.–90° C.

6. A process according to claim 5, wherein the pH of the solution is between about 10 to 11.

7. A process according to claim 4, wherein the pH of the solution is between about 8 to 11.

8. A process according to claim 4, wherein the oxidizing agent is chosen from among $NaNO_2$, $H_2O_2$ and air.

9. A process according to claim 1, wherein the polymeric material is of hydrophobic type and is chosen from among polystyrene, polychloromethylstyrene and polymethylmethacrylate.

10. A process according to claim 1, wherein said alkyl silicate is $Si(OEt)_4$.

11. A process according to claim 10, further comprising removing the inner polymeric material to produce a hollow shell.

12. A process according to claim 11, wherein the removal of the inner polymeric materials is accomplished by burning off or by dissolving off said polymeric material.

13. A process according to claim 12, wherein the temperature applied to when burn off the organic core of the microspheres is between 400° C. and 900° C.

14. A process according to claim 12, wherein the inner organic core of the microsphere is dissolved by using a solvent chosen from among toluene or dimethylformamide.

15. A process according to claim 1 or 11, further comprising the step of coupling ligands comprising one or more functional group(s) which are capable of linking other ligands to the silica layer.

16. A process according to claim 15, wherein the ligands form covalent bonds with the silica layer.

17. A process according to claim 16, wherein the ligands are chosen from among $SiCl_3(CH_2)_nX$, $Si(OR)_3(CH_2)_nX$, $OH(CH_2)_nX$, wherein R is an alkyl substituent, n is between 2 to 20 and X is $-NH_2$, $-CH_3$, $-CO_2R$, $-CN$.

18. A process according to claim 17, further comprising binding polyaldehyde ligands to the amino groups, on the coated microsphere surface.

19. A process according to claim 18, wherein residual amino groups on the surface of the said microsphere are blocked by suitable reagents.

20. A process according to claim 19, wherein the reagent is acetic acid N-hydroxysuccin-imide ester.

21. A process according to claim 19, further comprising coupling amino ligands to the polyaldehyde ligands bind on the coated microsphere surface.

22. A process according to claim 15, wherein the functional group is an amine group or other group which can be converted to amine group.

23. A process according to claim 1, wherein the microspheres are prepared by in situ polymerization.

24. A process according to claim 23, wherein the polymerization is carried out in the presence of a polymerization initiator.

25. A process according to claim 24, wherein the initiator is benzoylperoxide.

26. A process according to claim 1, wherein the hydrophilic surfactant is chosen from among polyvinylpyrrolidone, polyacrylic acid and polyethyleneoxide.

27. A polymeric microsphere, having a diameter of about 0.2 µm to 8 µm, comprising a surfactant on its surface, and coated with one or more layers of silica, wherein said silica coating consists of silica nanoparticles.

28. A microsphere according to claim 27, comprising one or more magnetic layers coupled to the surfactants, coated with a silica coating.

29. A hollow microsphere consisting of one or more shells of magnetic material and one or more silica shells.

30. A solid or hollow microsphere according to claim 28 and 29, further comprising ligands with one or more functional group(s) which are capable of linking other ligands, bound to the microsphere silica layer.

31. A microsphere according to claim 30, wherein the ligands comprise amine functional group or groups which may be converted to amine.

32. A microsphere according to claim 31, wherein the convertible group is a cyano, $-CN$.

33. A microsphere according to claim 30, wherein the ligands are chosen from among $SiCl_3(CH_2)_nX$, $Si(OR)_3(CH_2)_nX$, $OH(CH_2)_nX$, wherein R is an alkyl substituent, n is between 2 to 20 and X is selected from $-NH_2$, $-CH_3$, $-CO_2R$, and $-CN$.

34. A microsphere according to claim 33, comprising polyaldehyde ligands attached to said microspheres.

35. A microsphere according to claim 33, comprising polyaldehyde ligands covalently attached to the amine groups of the ligands bound to the microsphere silica layer.

36. A microsphere according to claim 35, wherein said polyaldehyde ligands are chosen from among glutaraldehyde and polyacrolein.

37. A microsphere according to claim 36, comprising amino ligands conjugated to said polyaldehyde.

38. A microsphere according to claim 37, wherein the amino ligands are chosen from among proteins, enzymes and antibodies.

39. A hollow microsphere consisting of one or more shells of silica nanoparticles.

40. A hollow or solid magnetic or nonmagnetic silica coated microsphere according to any one of the claims 27, 28, 29 or 39, for biological or medical applications.

41. A a microsphere according to claim 40, wherein said biological applications include cell labeling, cell separation and diagnostics.

* * * * *